(12) United States Patent
Troili et al.

(10) Patent No.: US 10,065,007 B2
(45) Date of Patent: Sep. 4, 2018

(54) BREATHING APPARATUS AND METHOD FOR SUPPORT VENTILATION

(75) Inventors: Carl-Erik Troili, Danderyd (SE); Mia Sköld, Sollentuna (SE)

(73) Assignee: Maquet Critical Care AB, Solna (SE)

( * ) Notice: Subject to any disclaimer, the term of this patent is extended or adjusted under 35 U.S.C. 154(b) by 1373 days.

(21) Appl. No.: 14/005,923

(22) PCT Filed: Mar. 18, 2011

(86) PCT No.: PCT/SE2011/050297
§ 371 (c)(1),
(2), (4) Date: Dec. 16, 2013

(87) PCT Pub. No.: WO2012/128674
PCT Pub. Date: Sep. 27, 2012

(65) Prior Publication Data
US 2014/0116439 A1   May 1, 2014

(51) Int. Cl.
*A61M 16/00* (2006.01)
*A61M 16/10* (2006.01)

(52) U.S. Cl.
CPC .... *A61M 16/0057* (2013.01); *A61M 16/0051* (2013.01); *A61M 16/0069* (2014.02); *A61M 16/024* (2017.08); *A61M 16/0066* (2013.01); *A61M 2016/0018* (2013.01); *A61M 2016/0021* (2013.01); *A61M 2016/0027* (2013.01); *A61M 2016/0039* (2013.01); *A61M 2230/63* (2013.01)

(58) Field of Classification Search
CPC .......... A61M 2016/0015; A61M 16/00; A61M 2016/0018; A61M 2016/0036; A61M 2016/0039; A61M 2016/0042; A61M 2016/0027; A61M 2016/0021
See application file for complete search history.

(56) References Cited

U.S. PATENT DOCUMENTS 5,598,838 A   2/1997   Servido et al.
5,803,066 A * 9/1998   Rapoport ............. A61B 5/0002
                                           128/204.21
(Continued)

FOREIGN PATENT DOCUMENTS

WO       97/06844      2/1997
WO     2008/100859     8/2008
(Continued)

*Primary Examiner* — Justine Yu
*Assistant Examiner* — Douglas Sul
(74) *Attorney, Agent, or Firm* — Schiff Hardin LLP

(57) ABSTRACT

In a method and breathing apparatus for providing support ventilation to a spontaneously breathing patient a pressure and/or a flow is monitored based on pressure and/or flow measurements, and efforts to inhale or exhale by the patient are detected based on changes in the monitored pressure and/or flow. When a change in the monitored pressure and/or flow indicating an effort to inhale or exhale is detected, the rate of that change is determined and used to calculate a suitable rate of change of pressure applied to the airways of the patient. By changing the applied pressure in accordance with the so determined suitable rate of change, the pressure rise time during inspiration and/or the pressure fall time during expiration can be adjusted to the needs of the patient to ensure efficient and comfortable ventilation.

15 Claims, 11 Drawing Sheets

(56) References Cited

U.S. PATENT DOCUMENTS

| | | | | |
|---|---|---|---|---|
| 5,865,173 | A * | 2/1999 | Froehlich | A61M 16/00 128/204.21 |
| 6,532,960 | B1 * | 3/2003 | Yurko | A61M 16/00 128/204.23 |
| 6,553,992 | B1 * | 4/2003 | Berthon-Jones | A61M 16/00 128/204.18 |
| 6,622,726 | B1 | 9/2003 | Du | |
| 6,626,175 | B2 * | 9/2003 | Jafari | A61M 16/00 128/204.18 |
| 7,137,389 | B2 | 11/2006 | Berthon-Jones | |
| 8,555,880 | B2 * | 10/2013 | Boring | A61M 16/0051 128/204.21 |
| 2006/0070624 | A1 | 4/2006 | Kane et al. | |
| 2008/0216832 | A1 * | 9/2008 | Carter | A61M 16/0051 128/204.21 |
| 2009/0007914 | A1 * | 1/2009 | Bateman | A61M 16/00 128/204.23 |
| 2009/0020119 | A1 | 1/2009 | Eger et al. | |

FOREIGN PATENT DOCUMENTS

| | | |
|---|---|---|
| WO | 2010/067236 | 6/2010 |
| WO | 2011/057362 | 5/2011 |

* cited by examiner

BREATHING APPARATUS AND METHOD FOR SUPPORT VENTILATION

FIELD OF THE INVENTION

The present invention relates to a breathing apparatus for providing support ventilation to a spontaneously breathing patient as well as to a method for providing pressure support ventilation to a spontaneously breathing patient as well as a storage medium encoded with programming instructions that cause such a method to be implemented in a computer-controlled manner.

DESCRIPTION OF THE PRIOR ART

Spontaneously breathing patients undergoing ventilator treatments may feel that the pressure rise time sometimes is too slow and sometimes too fast to be comfortable. In most breathing apparatuses according to prior art, the rise time in the system is fixed and set by the operator.

There are different definitions of pressure rise time in the art. Pressure rise time may be defined as the time it takes to increase the pressure from a positive end expiratory pressure (PEEP), or an expiratory positive airway pressure (EPAP), to an elevated target pressure, sometimes referred to as the inspiratory target pressure (ITP) or inspiratory positive airway pressure (IPAP). It may also be defined as the time during which the inspiratory pressure is increased with a certain amount, for example as the time during which the inspiratory pressure is increased from e.g. 10% to 90% of a maximum inspiratory pressure. No matter the definition, the pressure rise time can be seen as a measure of the inspiratory pressure increase rate, i.e. the rate at which the breathing apparatus increases the positive pressure applied to the patient during the initial phase of inspiration.

Similarly, the pressure fall time is a measure of the expiratory pressure decrease rate, i.e. the rate at which the breathing apparatus decreases the pressure against which the patient exhales during exhalation. Just like the pressure rise time, the pressure fall time is an important determinant of the perceived comfort of the ventilator treatment.

There are also breathing apparatuses according to prior art offering an adjustable rise time to increase patient comfort and/or the efficiency of the ventilator treatment.

U.S. Pat. No. 6,532,960 discloses an apparatus and method for a bi-level positive airway pressure support in which the rise time from the expiratory positive airway pressure to the inspiratory positive airway pressure is automatically controlled by the pressure support system. The apparatus monitors the patient's respiration to detect abnormal respiratory events, such as an apnoea, hypopnoea, upper airway resistance, snoring or other disturbances, and responds to the detected events by adjusting the rise time to maximize patient comfort.

U.S. Pat. No. 7,137,389 discloses an apparatus that provides for the determination of the instantaneous phase in the respiratory cycle of a subject. The apparatus permits breathing gas to be supplied to the subject in accordance with a pressure waveform, and includes an algorithm through which the rise time of a smooth pressure waveform can be automatically adjusted.

US 2009/00007914 discloses a method in a ventilator for reducing or eliminating upper airway obstruction, resistance or instability by adjusting the rise-time of the ventilator. This is achieved by continuously monitoring the shape of the inspiratory portion of the respiratory airflow, and adjusting the rise time upon detection of a shape indicative of the presence of upper airway obstruction, resistance or instability.

US 2009/0020119 discloses a process for operating a respirator, which makes possible improved respiration of patients suffering from different lung diseases. The method comprises the step of providing an inspiration pressure/time curve and flowing breathing gas into the patient according to this pressure/time curve. The curvature of the inspiration pressure/time curve is determined by a time constant which can be set by a physician or stored in the respirator. The time constant can be determined by means of the regression method and/or the occlusion method, or any other method known in the art.

WO 2010/067236 discloses a method for providing pressure support to a patient. The rise time between expiratory positive airway pressure (EPAP) and inspiratory positive airway pressure (IPAP) is adjusted in dependence of a measure associated with the inspiratory time of the patient. The measure may be the average inspiratory time, determined over one or a plurality of respiratory cycles, or during a predetermined time period.

US 2006/0070624 discloses a pressure support system delivering an inspiratory pressure having essentially a bi-level pressure waveform to the airways of a patient. The waveform alternates between an IPAP level and an EPAP level. The rise time from EPAP to IPAP may be adjusted to maximize patient comfort. During an inspiration phase, the inspiratory flow is measured and used to estimate a predicted flow which is compared with a desired target flow. If the predicted flow exceeds the target flow the rise time is changed.

U.S. Pat. No. 5,598,838 discloses a pressure support ventilator permitting explicit control of rise time to accommodate the comfort of the patient. The rise time can be set by an operator of the ventilator via a control panel. The fall time is set at 25% of the rise time or 100 milliseconds, whichever is greater.

Another document addressing the problem of increasing patient comfort during pressure-controlled support ventilation is U.S. Pat. No. 6,622,726. This document discloses a positive airway pressure assist apparatus that supplies gas to a patient according to a pre-set target pressure. The apparatus is configured to determine a level of patient breathlessness at periodic intervals and to calculate a boost pressure above the pre-set target pressure based on the determined breathlessness level. The apparatus is further configured to boost the pressure in the sense of increasing its magnitude over the target pressure during a first part of the inspiratory phase, and to decrease the pressure back to the target pressure prior to the end of the inspiratory phase.

Although many of the techniques proposed by these documents serve to increase patient comfort and/or the efficiency of the treatment, there is still a desire to further improve the patient's perceived experience of pressure support ventilation. In particular, it is a desire to tailor the treatment to the needs of the patient.

SUMMARY OF THE INVENTION

It is an object of the present invention to improve patient comfort in supported ventilation.

This and other objects are achieved by a breathing apparatus for providing support ventilation to a spontaneously breathing patient, that includes a pressure regulator that regulates a pressure applied to the airways of the patient, at least one pressure and/or flow sensor for obtaining pressure and/or flow measurements, and a control unit for monitoring a pressure and/or flow based on the measurements. The control unit is configured to detect an effort by the patient to inhale or exhale based on a change in the monitored pressure and/or flow. The control unit is further configured to determine a suitable rate of change in the pressure applied to the patient based on the rate of the change in the monitored pressure and/or flow, and to control the pressure regulator to change the applied pressure in accordance with said suitable rate of change in response to said effort to inhale or exhale.

In other words, the breathing apparatus is adapted to monitor a pressure and/or flow, and, when a change in the monitored pressure and/or flow indicating an effort to inhale or exhale is detected, to change the pressure applied to the patient in accordance with a rate of change that is determined by the rate of the change in pressure and/or flow that triggered the change in applied pressure.

By determining the rate of change of the pressure that is to be applied to the patient based on the rate of change of the monitored pressure and/or flow, the pressure applied to the patient can be tailored to the patient's instantaneous need for breathing gas. If the rate of change of the monitored parameter (i.e. pressure and/or flow) is high, the patient has made a strong effort to inhale or exhale and is hence assumed to desire a quick inspiration or expiration. If, on the other hand, the rate of change of the monitored parameter is low, the patient has made a weaker effort to inhale or exhale, whereupon the breathing apparatus provides for a gentle and more drawn-out inspiration or expiration. Consequently, the rate of change in applied pressure may always be tailored to the patient's effort to inhale or exhale. Thereby, the patient will be subject to an efficient but yet lenient and comfortable support ventilation.

The control unit may be configured to establish that the patient has made an effort to inhale or exhale by determining when the monitored pressure and/or flow meets one or several conditions. The condition may be a threshold value for the monitored pressure and/or flow. It may also be a threshold value for a change in a rate of change of the monitored pressure and/or flow. The control unit may also be configured to analyse both changes in magnitude of the monitored pressure and/or flow, and changes in the rate of change of the monitored pressure and/or flow, and to use them both in the determination as to whether an effort to inhale or exhale has been made by the patient.

The point in time at which the breathing apparatus establishes that the patient has made an effort to inhale or exhale will hereinafter be referred to as the trigger point. The trigger point can be said to be the point in time at which the breathing apparatus notices that the patient wants to go from one respiratory phase to another, i.e. from an inspiratory phase to an expiratory phase or vice versa. The breathing apparatus is preferably configured to change the pressure applied to the patient at or just after the trigger point in accordance with a rate of change that is determined based on a rate of change of the monitored pressure and/or flow at or just before the trigger point.

To this end, the control unit may be configured to establish a first point in time when a change in the monitored pressure and/or flow exceeds a first predefined threshold value indicating that the patient may have started an effort to inhale or exhale, and a second point in time when said change exceeds a second predefined threshold value verifying that the patient has started an effort to inhale or exhale. The control unit may be configured to determine the suitable rate of change in applied pressure based on the time elapsed between the first and second points in time, which time is indicative of the rate of change in the monitored pressure and/or flow and hence of the patient's effort to inhale or exhale.

The monitored pressure and/or flow may be the flow and/or pressure measured by the at least one pressure and/or flow sensor. However, it may also be a pressure and/or flow that is calculated by the control unit based on the measurements received by the at least one pressure and/or flow sensor.

In one embodiment, the monitored pressure and/or flow is a proximal pressure substantially corresponding to the airway pressure of the patient. The proximal pressure may be measured by a pressure sensor arranged in a Y-piece connecting the patient to the breathing apparatus in a manner well known in the art. In this embodiment, the pressure measurements obtained by the same sensor may be used by the control unit to control the pressure regulating means such that the suitable rate of change in the pressure applied to the patient is obtained.

In another embodiment, the monitored pressure and/or flow is a proximal flow substantially corresponding to the flow through the airways of the patient. The proximal flow may be measured by a flow sensor arranged in the Y-piece, or one or more flow sensors arranged in the inspiratory line and/or expiratory line. Monitoring a flow instead of a pressure may be advantageous in that also weak efforts to inhale or exhale can be detected by the control unit. If monitoring a pressure, weak efforts to inhale or exhale may be hard to detect since the change in pressure caused by an effort to inhale or exhale may be very small compared to the applied pressure.

Preferably, the control unit is configured to monitor both a pressure and a flow and to use changes in the pressure and/or flow in the determination of the suitable rate of change in the pressure that is to be applied to the patient at or just after the trigger point.

The rate of change in pressure or flow corresponds to the derivative of the pressure or flow curve. Consequently, the breathing apparatus can be said to be adapted to determine a derivative for the pressure curve that is to be applied to the patient at or just after the trigger point based on the derivative of the monitored pressure and/or flow curve at or just before the trigger point. Hereinafter, the part of the monitored pressure or flow curve that is indicative of the patient's effort to inhale or exhale will sometimes be referred to as the patient effort indicator (PEI). If the PEI is indicative of the patient's effort to inhale it will be referred to as $PEI_{insp}$ while, if the PEI is indicative of the patient's effort to exhale, it will be referred to as the $PEI_{exp}$.

The breathing apparatus according to the invention may hence be adapted for patient triggered support ventilation in the conventional meaning of starting to increase/decrease the pressure applied to the patient when a change in a monitored pressure and/or flow indicating the patient's effort to inhale/exhale is detected. However, it is also adapted for an enhanced type of patient triggered pressure support ventilation in which the rate of pressure increase/decrease is adapted to the patient's effort to inhale/exhale.

The breathing apparatus may be adapted to provide the patient triggered support ventilation in either or both of pressure support mode and volume support mode.

In pressure support mode, during inspiration, the breathing apparatus increases the pressure applied to the airways of the patient until a certain target pressure is reached. Typically, this is achieved by measuring a proximal pressure substantially corresponding to the airway pressure of the patient, and increasing the pressure applied to the airways of the patient until the proximal pressure reaches a preset target pressure. This target pressure is then maintained until the patient's effort to exhale is detected. During expiration, the breathing apparatus decreases the pressure until a preset expiratory target pressure, often referred to as the positive end-expiratory pressure (PEEP), is reached.

In volume support mode, during inspiration, the breathing apparatus increases the pressure applied to the airways of the patient until a certain target volume of breathing gas has been supplied to the patient (the preset tidal volume). This may be achieved by measuring the flow supplied to the patient, e.g. by means of a flow sensor in the Y-piece or the inspiratory line, and integrating the flow to calculate the supplied volume of breathing gas. Normally, volume support mode only offers patient triggered inspiration. The expiratory phase is normally not initiated by the patient but typically starts when the preset tidal volume is delivered. However, patient triggered expiration may be offered also in volume support mode. For example, the breathing apparatus may be configured to interrupt the flow of breathing gas supplied to the patient when the preset tidal volume has been delivered, and to maintain the airway pressure of the patient at this point in time, e.g. by regulating an expiratory valve of the breathing apparatus. This end inspiratory pressure (which may vary from breath to breath) may be maintained until the patient's effort to exhale is detected. During expiration, the breathing apparatus may be configured to decrease the pressure applied to the airways of the patient until either a preset end expiratory target pressure is reached, or until a certain volume of exhalation gas has been expired.

In both pressure mode and volume mode, the rate of pressure increase during inspiration and/or the rate of pressure decrease during expiration may be determined in accordance with the principles described above.

The breathing apparatus may be configured to detect a change in the monitored pressure and/or flow during a final phase of an expiratory phase, which change indicates an effort to inhale by the patient, and to support inspiration by increasing the pressure applied to the patient with a rate that is determined based on the rate of the change in monitored pressure and/or flow caused by the effort to inhale. This means that the breathing apparatus is adapted to determine the rate at which the inspiratory pressure should be increased, i.e. the inspiratory pressure increase rate, based on a rate of change in the monitored pressure and/or flow during the final phase of an expiratory phase.

Likewise, the breathing apparatus may be configured to detect a change in the monitored pressure and/or flow during a final phase of an inspiratory phase, which change indicates an effort to exhale by the patient, and to support expiration by decreasing the pressure applied to the patient with a rate that is determined based on the rate of the change in monitored pressure and/or flow caused by the effort to exhale. This means that the breathing apparatus is adapted to determine the rate at which the expiratory pressure should be decreased, i.e. the expiratory pressure decrease rate, based on the rate of change in the monitored pressure and/or flow during the final phase of an inspiratory phase.

Referring to the background portion, this means that the breathing apparatus may be configured to adjust either or both of the pressure rise time and the pressure fall time based on the rate of change of the monitored pressure and/or flow at or just before the trigger point.

Preferably, the breathing apparatus is configured to calculate the suitable inspiratory pressure increase rate and/or the expiratory pressure decrease rate on a breath-by-breath basis. This means that the pressure increase rate for any given inspiratory phase is calculated based on the rate of the change in monitored pressure and/or flow that triggered that particular inspiratory phase, i.e. based on the rate of change in monitored pressure and/or flow during the final phase of the expiratory phase directly preceding the inspiratory phase. In the same way, for each expiratory phase, the suitable expiratory pressure decrease rate may be calculated based on the rate of the change that triggered that particular expiratory phase.

The suitable rate of change in the applied pressure may be either constant or variable. A constant inspiratory pressure increase rate implies that the inspiratory pressure curve has a constant positive slope while a variable inspiratory pressure increase rate implies that the inspiratory pressure curve is curved. Likewise, a constant expiratory pressure decrease rate implies that the expiratory pressure curve has a constant negative slope.

In an exemplary implementation of the invention, the breathing apparatus may be configured to calculate a constant rate of change in applied pressure that is proportional to the rate of change of the monitored flow and/or pressure. Taking the inspiratory phase as an example, this may be achieved by determining a derivative that is indicative of a first slope of the monitored pressure and/or flow curve at or just before the inspiratory trigger point, and to apply an inspiratory pressure at or just after the inspiratory trigger point following a curve having a constant slope that is proportional to said first slope. In other words, the breathing apparatus may be configured to calculate an inspiratory pressure increase curve having a constant derivative that is proportional to the or a derivative of $PEI_{insp}$. However, there need not to be a mathematical relationship between the suitable rate of change of applied pressure and the rate of change of the monitored pressure and/or flow. The breathing apparatus may be configured to store a look-up table wherein different rates of change of the monitored pressure and/or flow are associated with different suitable rates of change in applied pressure. The breathing apparatus may be configured to determine a rate of change of the monitored pressure and/or flow, look up which suitable rate of change of applied pressure is associated with that rate of change of monitored pressure and/or flow in the look-up table, and change the applied pressure in accordance with that suitable rate of change.

In another exemplary embodiment, the breathing apparatus is configured to determine the suitable rate of change in the applied pressure also based on at least one change in the rate of change of the monitored pressure and/or flow. This means that the breathing apparatus may be configured to determine a second order derivative of the monitored pressure and/or flow curve at or just before the trigger point, i.e. a second derivative of $PEI_{insp}$ or $PEI_{exp}$, and to use also this second order derivative in the determination of the suitable rate of change in applied pressure. This is advantageous in that also the second derivative of the PEIs reveals important information of the patient's effort to inhale or exhale, e.g. whether the patient's effort to inhale or exhale increases or decreases over time.

The breathing apparatus may also be configured to calculate a variable rate of change in the pressure applied to the patient. For example, the control unit may be configured to control the pressure regulating means to maintain a substantially constant expiratory target pressure level at the end of the expiratory phase and at a substantially constant inspiratory target pressure level being higher that said expiratory target pressure level at the end of the inspiratory phase, and to calculate a variable inspiratory pressure increase rate accelerating in the initial phase of the inspiratory phase and/or decelerating when approaching said inspiratory target pressure level. This results in smoother and less abrupt pressure support ventilation, thus further increasing the comfort of the ventilator treatment. The breathing apparatus may be configured to calculate an accelerating and/or decelerating expiratory pressure decrease rate in a similar manner.

In a preferred embodiment of the invention, the breathing apparatus is configured to determine the suitable rate of change in applied pressure prior to the trigger point so as to be able to change the applied pressure with the suitable rate of change directly upon detection of the trigger point, without having to determine the suitable rate of change after detecting the trigger point. This is advantageous in that the breathing apparatus will respond quicker to the patient's effort to inhale or exhale and hence further increase the comfort of the treatment.

The object is also achieved by a method for providing support ventilation to a spontaneously breathing patient. The method comprises the steps of:
- monitoring a pressure and/or flow based on pressure and/or flow measurements obtained by means of at least one pressure and/or flow sensor;
- detecting an effort by the patient to inhale or exhale based on a change in the monitored pressure and/or flow;
- determining a suitable rate of change in a pressure applied to the airways of the patient based on the rate of the change in monitored pressure and/or flow, and
- changing the applied pressure in accordance with said suitable rate of change in response to said effort to inhale or exhale.

The object is also achieved by a computer program comprising computer-readable code which, when executed by a processing means in a breathing apparatus, causes the breathing apparatus to perform the above mentioned method.

The computer program may be stored on a digital storage medium, such as an internal memory of said breathing apparatus, a hard disk drive, a CD ROM, or the like.

The computer program may be offered for installation on existing breathing apparatuses to make them capable of performing the above mentioned method.

More advantageous embodiments of the breathing apparatus, method and computer program will be described in the detailed description following hereinafter.

BRIEF DESCRIPTION OF THE DRAWINGS

A more complete appreciation of the invention disclosed herein will be obtained as the same becomes better understood by reference to the following detailed description when considered in conjunction with the accompanying figures briefly described below, in which drawings the same reference numerals are used to represent the same functional elements.

DESCRIPTION OF THE PREFERRED EMBODIMENTS

Figure 1:
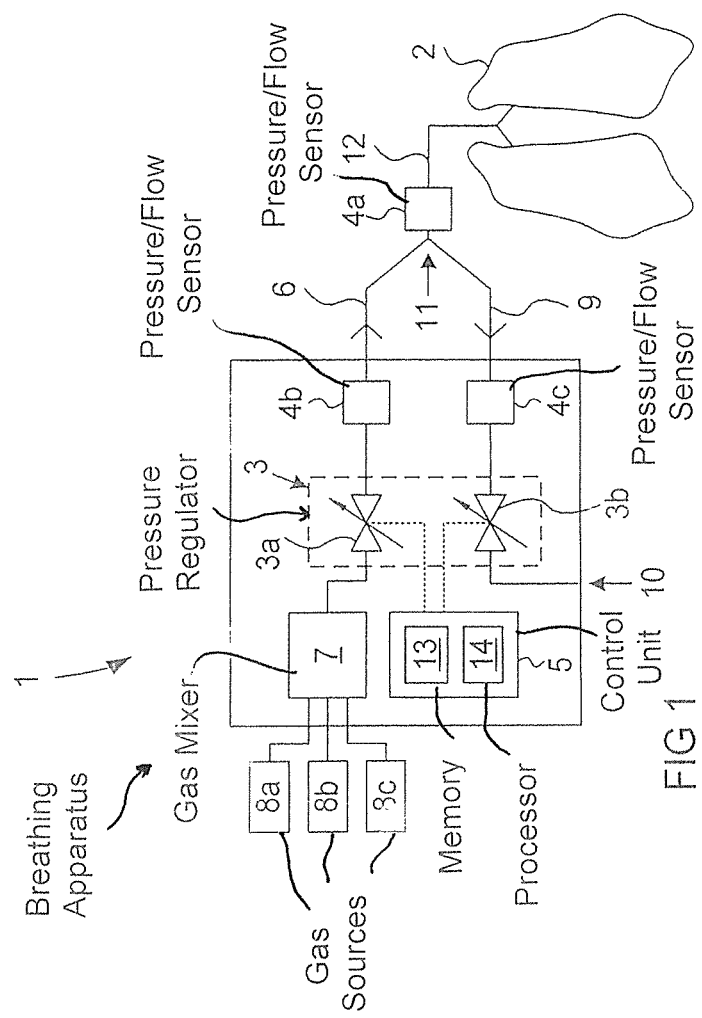
FIG. 1 illustrates a breathing apparatus according to one embodiment of the invention.

FIG. 1 illustrates a breathing apparatus 1 in form of a ventilator for providing support ventilation to a spontaneously breathing patient 2, illustrated by a pair of lungs. The breathing apparatus 1 is configured to be operated in either pressure support mode or volume support mode.

The breathing apparatus 1 has a pressure regulator 3 arranged to apply a pressure to the airways of the patient 2. The breathing apparatus 1 further has at least one pressure and/or flow sensor 4a-4c for obtaining pressure and/or flow measurements. Furthermore, the breathing apparatus comprises a control unit 5 for monitoring a pressure and/or flow based on the pressure and/or flow measurements obtained by the pressure and/or flow sensors 4a-4c, and for controlling the pressure regulating means 3 based on the monitored pressure and/or flow.

In this embodiment, the pressure regulator 3 includes a controllable inspiratory valve 3a for regulating the pressure applied to the airways of the patient 2 during inspiration, and a controllable expiratory valve 3b for regulating the pressure applied to the airways of the patient 2 during expiration. It should be appreciated that the pressure regulator 3 could be realized in many different ways. For example, the inspiratory valve 3a may be exchanged for a blower or any other means capable of applying a controlled pressure to the airways of a patient.

During inspiration, the control unit 5 controls the inspiratory valve 3a to regulate the pressure applied to the airways of the patient 2 by regulating a flow of breathing gas supplied to the patient via an inspiratory line 6. The breathing apparatus 1 further includes a gas mixer 7 coupled to one or more internal or external gas sources 8a-8c for the supply of pressurised breathing gas.

During expiration, the control unit 5 controls the expiratory valve 3b to regulate the pressure applied to the airways of the patient 2 by regulating a flow of exhalation gases exhaled by the patient via an expiratory line 9. The exhalation gases are then vented out to ambient air or a scavenging system through a vent 10 of the breathing apparatus 1.

The setup of pressure and/or flow sensors 4a-4c may vary in dependence of the intended function of the breathing apparatus 1. The breathing apparatus 1 should include at least one pressure and/or flow sensor operable to measure a pressure and/or flow that is indicative of the patient's efforts to inhale and/or exhale. A single pressure or flow sensor located in a Y-piece 11 connecting the inspiratory line 6 and expiratory line 9 with a patient connector 12 is sufficient to practice the invention. However, in order for the breathing apparatus 1 to be operated in both pressure support mode and volume support mode, and in order to sense also weak efforts to inhale or exhale made by the patient, more sensors may be desired.

In a preferred embodiment, the breathing apparatus has a pressure sensor 4a arranged in or close to the Y-piece 11 to measure a proximal pressure substantially corresponding to the airway pressure of the patient 2, and two flow sensors 4b and 4c arranged in the inspiratory line 6 and expiratory line 9, respectively, to measure the flow of gas inhaled and exhaled by the patient 2. Although not shown in the drawing it should be appreciated that the sensors 4a-4c are connected to the control unit 5 in order for the control unit to control the pressure regulating means 3 based on pressure and/or flow values directly obtainable through the sensors 4a-4c, and/or derivable by the control unit 5 from the measured values.

As will be described in further detail below, the control unit 5 is configured to detect when the patient 2 wants to go from one respiratory phase to the other, i.e. from inspiration to expiration or vice versa, and to switch respiratory phase accordingly. This means that the breathing apparatus 1 is adapted for patient triggered support ventilation. However, the control unit 5 is also operable to support a novel and enhanced type of patient triggered support ventilation by establishing whether the patient 2 seems to desire a quick or slow inspiration/expiration, and to control the function of the breathing apparatus 1 to satisfy the desire of the patient.

To this end, the control unit 5 is configured to monitor a pressure and/or flow based on the pressure and/or flow measurements obtained by means of at least one of the sensors 4a-4c, and to detect an effort by the patient 2 to inhale or exhale based on a change in the monitored pressure and/or flow. Based on the rate of the change in the monitored pressure and/or flow, the control unit 5 determines a suitable rate of change, i.e. a target rate of change, for the pressure applied to the airways of the patient, and controls the pressure regulating means 3 to change the applied pressure (i.e. the pressure applied to the airways of the patient) in accordance with the so determined suitable rate of change, in response to said effort to inhale or exhale. This functionality is typically provided by means of a computer program stored on a memory 13 in the control unit 5, which computer program causes the control unit to perform the above described actions when executed by a processor 14 of the control unit 5. The computer program may also be installed on an external computer which may be connected to the control unit 5 of the breathing apparatus 1 to make it perform said actions, thereby making the breathing apparatus 1 capable of providing the enhanced type of patient triggered support ventilation described herein.

With reference now made to FIGS. 2 to 8, description will be made of exemplary embodiments illustrating how a monitored pressure or flow can be used to achieve the above mentioned enhanced patient triggered support ventilation by adapting the inspiratory and expiratory pressure curves (i.e. the pressure applied to the airways of the patient during inspiration and expiration, respectively) to the needs of the patient. When describing FIGS. 2 to 8, simultaneous reference will be made to the breathing apparatus 1 in FIG. 1.

Figure 2:
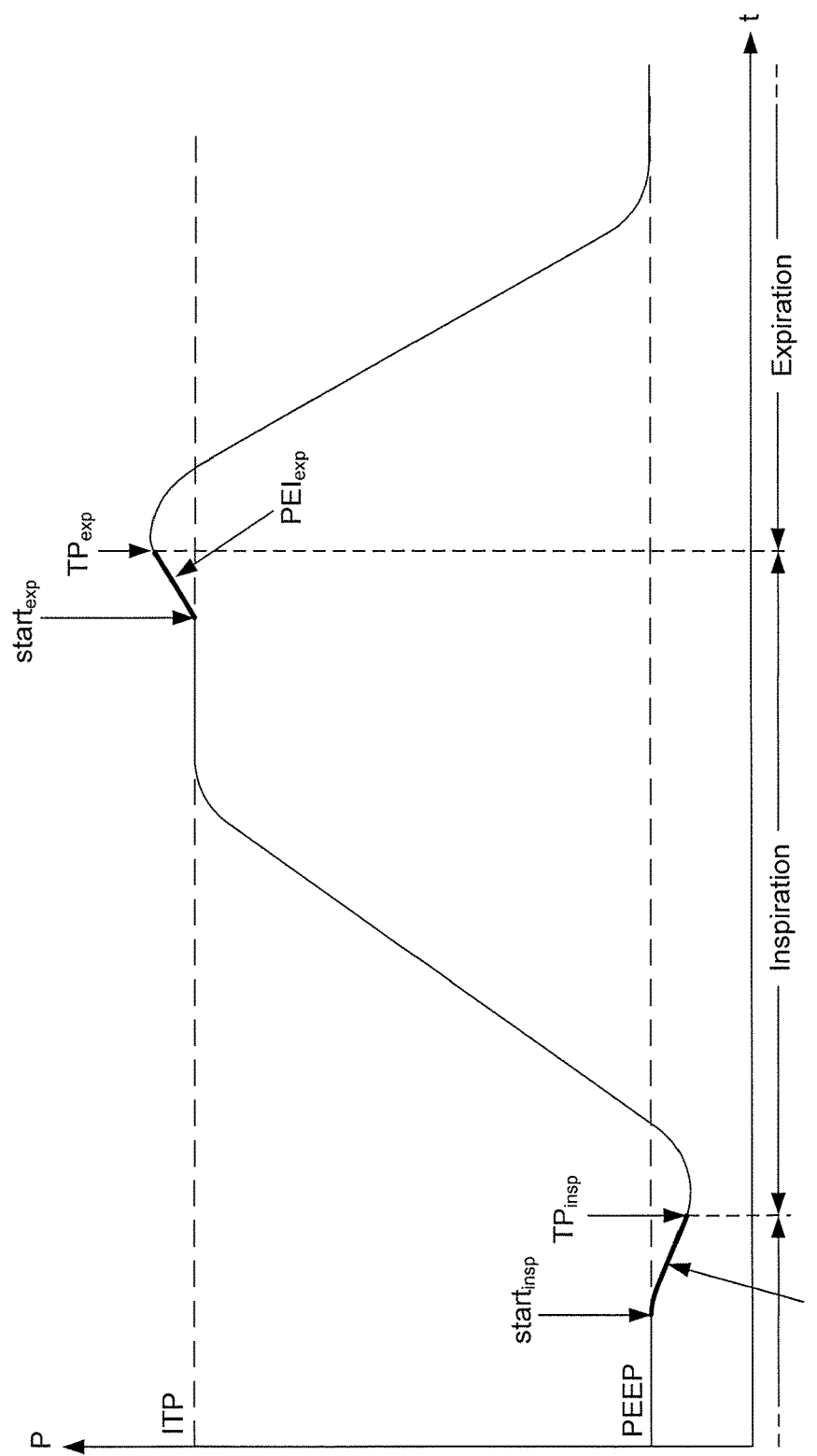
FIGS. 2-6 all illustrate pressure curves and parts of pressure curves and the principles of controlling the rate of change in the pressure to be applied to the airways of the patient at or just after the trigger point based on a rate of change of a monitored pressure at and/or prior to the trigger point.

FIG. 2 illustrates a pressure/time curve, hereinafter simply referred to as pressure curve, representing a measured or calculated pressure substantially corresponding to the airway pressure of a patient undergoing pressure supported ventilation. The pressure may for example be the proximal pressure measured by the pressure sensor 4a during a respiratory cycle. Here, it is seen that the control unit 5 of the breathing apparatus 1 is adapted to control the pressure regulating means 3 to maintain a substantially constant expiratory target pressure level, or positive end-expiratory pressure (PEEP), at the end of the expiratory phase, and to maintain the pressure at a substantially constant inspiratory target pressure (ITP) at the end of the inspiratory phase. The PEEP and ITP levels may be set by an operator of the breathing apparatus 1, or calculated by the control unit 5 based on patient-related parameters and/or measured values.

At a certain point in time, start$_{insp}$, during the final phase of expiration, the patient makes an effort to inhale. The effort to inhale introduces a change in the monitored pressure. In this case where the pressure is the proximal pressure measured in the Y-piece 11 of the breathing apparatus 1, the change in monitored pressure is a decrease in pressure. The control unit 5 of the breathing apparatus is configured to determine when the monitored pressure fulfils an inspiratory trigger condition, and, when the inspiratory trigger condition is fulfilled, start the inspiration phase by increasing the pressure applied to the airways of the patient 2. The point in time, TP$_{insp}$, at which the control unit 5 detects that the inspiratory trigger condition is fulfilled is the inspiratory trigger point. As will be described in greater detail below, the inspiratory trigger condition may for example be a threshold value for the monitored pressure.

Thus, when the control unit 5 can verify that an effort to inhale has been made by the patient, it supports the inhalation attempt by increasing the pressure applied to the airways of the patient 2. The control unit 5 is further configured to determine the rate of the pressure increase based on the rate of the pressure decrease at or just before the inspiratory trigger point, TP$_{insp}$, which pressure decrease is caused by the patient's effort to inhale. To this end, the control unit 5 is configured to analyse the pressure curve segment between the point in time, start$_{insp}$, at which the patient 2 starts to inhale and the inspiratory trigger point, TP$_{insp}$, at which the control unit 5 establishes that the patient has made an effort to inhale, and to determine the inspiratory pressure increase rate based on the slope and/or curvature of this pressure curve segment. The pressure curve segment between the point in time, start$_{insp}$, at which the patient 2 starts to inhale and the inspiratory trigger point, TP$_{insp}$, (possibly including one or both end points) is hence used by the control unit 5 as an indicator of the effort to inhale made by the patient and will hereinafter be referred to as the PEI$_{insp}$ or the PEI$_{insp}$ curve, where PEI is short for Patient Effort Indicator.

Similarly, during the final phase of inspiration, the patient 2 makes an effort to exhale at a point in time, start$_{exp}$. In this case where the pressure is the proximal pressure measured in the Y-piece 11 of the breathing apparatus 1, the effort to exhale may cause an increase in the monitored pressure. The control unit 5 of the breathing apparatus 1 is configured to determine when the monitored pressure fulfils an expiratory trigger condition, and, when the expiratory trigger condition is fulfilled, start the expiration phase by decreasing the pressure applied to the airways of the patient 2. The point in time, TP$_{exp}$, at which the control unit 5 detects that the expiratory trigger condition is fulfilled is the expiratory trigger point. The expiratory trigger condition may for example also be a threshold value for the monitored pressure.

Upon detection of the expiratory trigger point, TP$_{exp}$, the control unit 5 switches from the inspiratory phase to the expiratory phase by decreasing the pressure applied to the airways of the patient 2 so as to support the exhalation attempt made by the patient. The control unit 5 is configured to determine the rate of pressure decrease based on the rate of the pressure increase at or just before the expiratory trigger point, TP$_{exp}$, which increase is caused by the patient's effort to exhale. In a way similar to the way the inspiratory pressure curve is determined, the control unit 5 analyses the pressure curve segment between the point in time, start$_{exp}$, at which the patient 2 starts to exhale and the expiratory trigger point, TP$_{exp}$, at which the control unit 5 can verify that the patient really has made an effort to exhale, and determines the expiratory pressure decrease rate based on the slope and/or curvature of this pressure curve segment. The pressure curve segment between the point in time, start$_{exp}$, at which the patient 2 starts to exhale and the expiratory trigger point, TP$_{exp}$, (possibly including one or both end points) is hence used by the control unit 5 as an indicator of the effort to exhale made by the patient and will hereinafter be referred to as the $PEI_{exp}$, or $PEI_{exp}$ curve.

Figure 3:
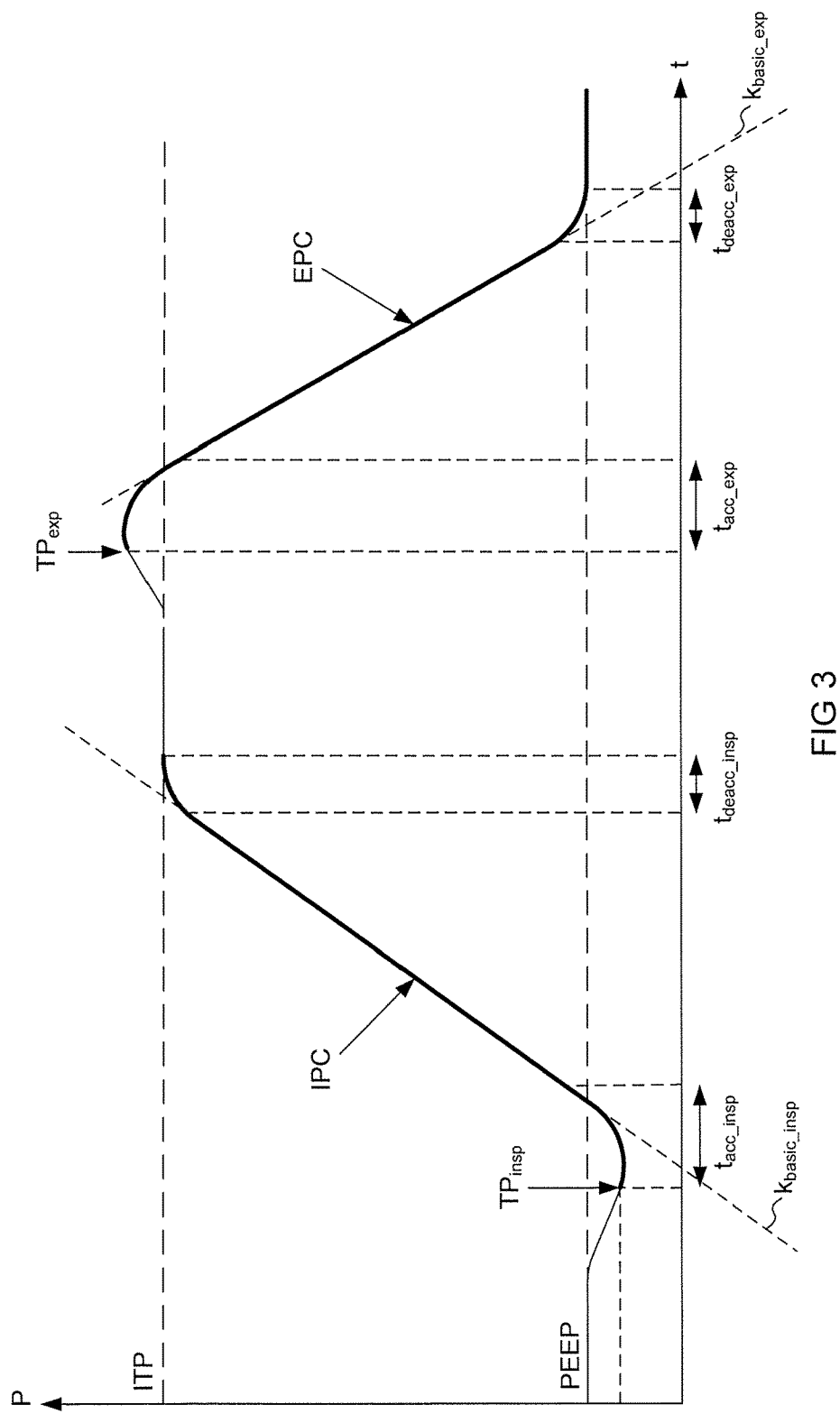

With simultaneous reference now made to FIGS. 1, 2 and 3, this means that the control unit 5 of the breathing apparatus 1 is adapted to determine the slope and/or curvature of an inspiratory pressure curve (IPC) based on the slope and/or curvature of the $PEI_{insp}$ curve, and to determine the slope and/or curvature of an expiratory pressure curve (EPC) based on the slope and/or curvature of $PEI_{exp}$ curve.

The control unit 5 is configured to analyse the $PEI_{insp}$ and $PEI_{exp}$ curves and to determine, for the respective curve, at least one value that is indicative of the rate of change in the monitored quantity, which in this example is the proximal pressure substantially corresponding to the airway pressure of the patient 2. The control unit 5 then calculates a suitable inspiratory pressure increase rate and a suitable expiratory pressure decrease rate based on said values and controls the pressure regulating means 3 to increase the inspiratory pressure and decrease the expiratory pressure with said suitable inspiratory pressure increase rate and said suitable expiratory pressure decrease rate.

Based on the above mentioned values, the control unit 5 may be adapted to determine a basic inspiratory pressure increase rate, $k_{basic\_insp}$, and a basic expiratory pressure decrease rate, $k_{basic\_exp}$. The control unit 5 may further be adapted to control the pressure regulating means 3 to regulate the inspiratory pressure applied to the airways of the patient such that the inspiratory pressure curve becomes fitted to the basic inspiratory pressure increase rate, $k_{basic\_insp}$. This means that the inspiratory pressure curve will have an average slope corresponding to the basic inspiratory pressure increase rate, $k_{basic\_insp}$. Likewise, the expiratory pressure curve can be adjusted so that its average slope corresponds to the basic expiratory pressure decrease rate, $k_{basic\_exp}$.

In one embodiment, the inspiratory and expiratory pressure curves may be substantially linear, meaning that the inspiratory pressure increase rate and the expiratory pressure decrease rate are substantially constant and equal to the basic inspiratory pressure increase rate, $k_{basic\_insp}$, and basic expiratory pressure decrease rate, $k_{basic\_exp}$, respectively.

However, in order to make the transition between the respiratory phases smoother and more comfortable to the patient 2, the inspiratory and expiratory pressure curves are preferably smooth curves. This means that the rate of change in the pressure applied to the airways of the patient preferably accelerates in the initial phase of inspiration and expiration, and decelerates when approaching the inspiratory target pressure level and the PEEP level, respectively.

In the exemplary embodiment illustrated in FIG. 3, the control unit 5 is adapted to, upon detection of the inspiratory trigger point, $TP_{insp}$, control the pressure regulating means 3 to apply a pressure to the airways of the patient 2 having an accelerating pressure increase rate for a certain period of time, face This period of time, $t_{acc\_insp}$, may be a parameter that is preset by the operator of the breathing apparatus 1 or calculated by the control unit 5 based on the slope and/or curvature of $PEI_{insp}$. In the same way, the time period, $t_{acc\_exp}$, for acceleration of the pressure decrease rate during the initial phase of expiration may be a preset parameter or calculated by the control unit 5 based on the slope and/or curvature of $PEI_{exp}$. The same applies to the time periods, $t_{deacc\_insp}$, $t_{deacc\_exp}$, for deceleration of the rate of change of pressure increase and decrease during inspiration and expiration, respectively.

Figure 4:
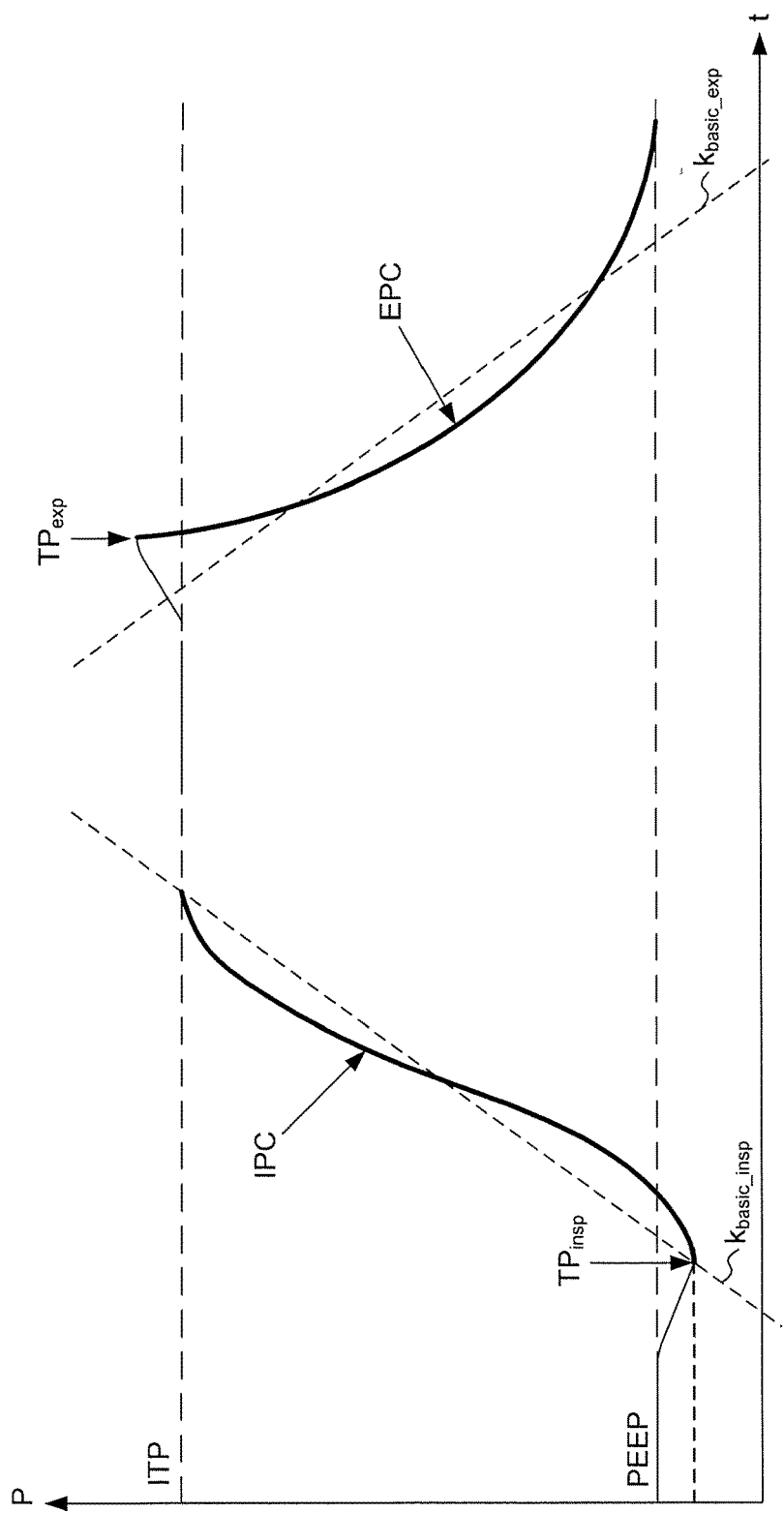

The inspiratory and expiratory pressure curves may also have other shapes. For example, the inspiratory pressure and the expiratory pressure applied to the patient after detection of the effort to inhale and exhale, respectively, may be determined by a polynomial or an exponential function. FIG. 4 illustrates an embodiment in which the control unit 5 of the breathing apparatus 1 is configured to determine polynomial inspiratory and expiratory pressure curves. The control unit 5 of the breathing apparatus 1 may for example be configured to determine a basic inspiratory pressure increase rate, $k_{basic\_insp}$, based on the slope and/or curvature of $PEI_{insp}$, and to fit a polynomial inspiratory pressure curve to the basic inspiratory pressure increase rate. Angle and/or curvature constraints can be added as end conditions in the curve fitting computation to ensure a smooth transition from the PEEP level to the ITP level. Likewise, a polynomial expiratory pressure curve can be calculated based on the basic expiratory pressure decrease rate, $k_{basic\_exp}$, together with end conditions ensuring a smooth transition from the ITP level to the PEEP level. In the illustrated scenario, the inspiratory pressure curve is a third degree polynomial curve whereas the expiratory pressure curve is a second degree polynomial curve.

Figure 5:
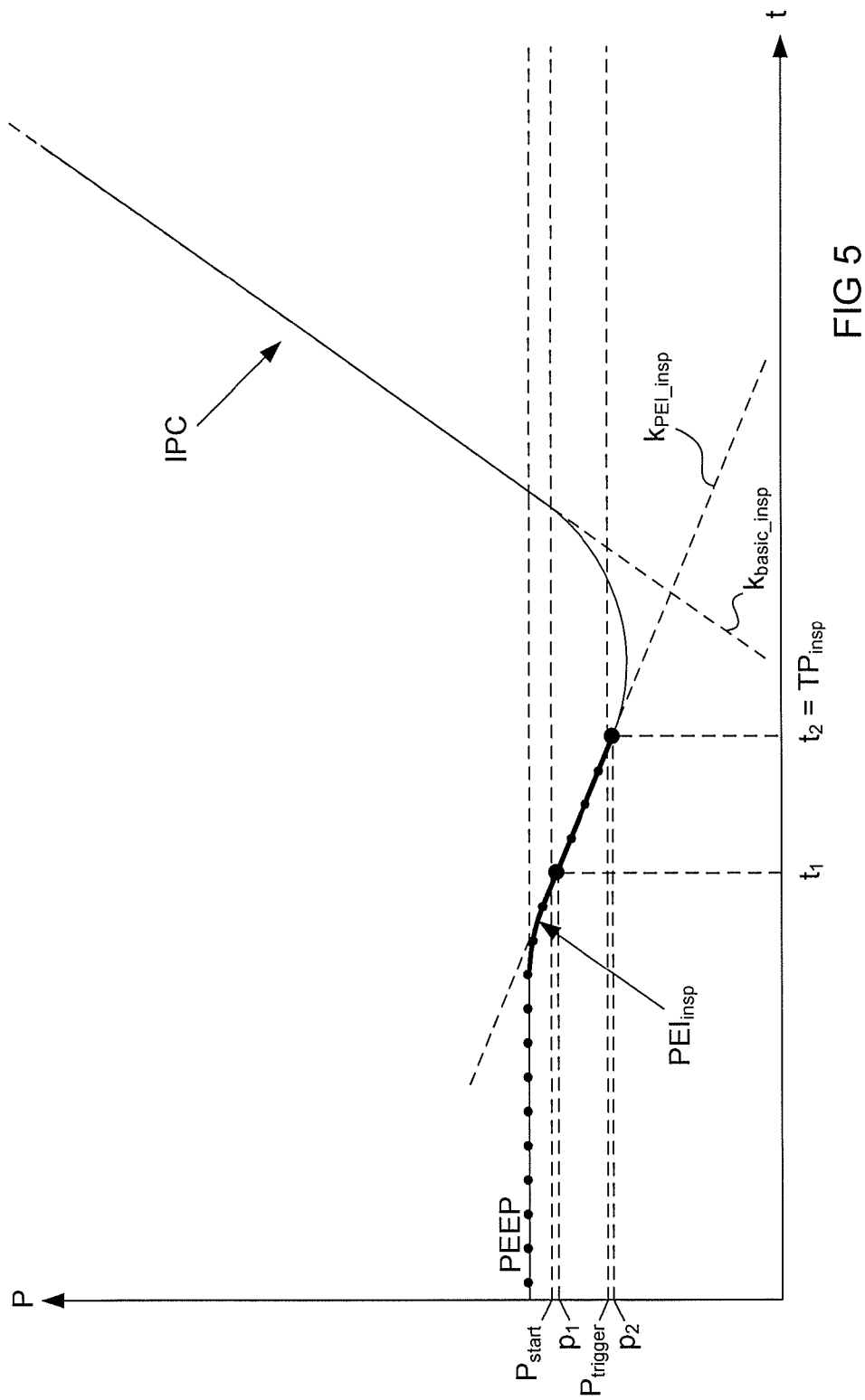

FIG. 5 illustrates the pressure curve illustrated in FIG. 3 during the final phase of expiration and the initial phase of inspiration. The dots along the pressure curve illustrate sampled pressure values, obtained by the pressure sensor 4a of the breathing apparatus 1 illustrated in FIG. 1, and registered by the control unit 5.

During the final phase of expiration the control unit 5 compares each sampled pressure value with a first pressure threshold value, $P_{start}$. At a first point in time, $t_1$, a sampled pressure value, $p_1$, falls below the first pressure threshold value, $P_{start}$, indicating to the control unit 5 that the patient 2 may have started an effort to inhale. In this exemplary embodiment, the trigger condition is a second pressure threshold value, $P_{trigger}$. At a second point in time, $t_2$, another sampled pressure value, $p_2$, falls below the second pressure threshold value, $P_{trigger}$, indicating to the control unit 5 that the pressure drop really seems to be caused by an effort to inhale by the patient. This second point in time, $t_2$, hence corresponds to the inspiratory trigger point, $TP_{insp}$.

In one embodiment of the invention, the control unit 5 may be configured to determine the rate of change in the monitored pressure by calculating the slope, $k_{PEI\_insp}$, of the $PEI_{insp}$ curve as:

$$k_{PEI\_insp}=(p_2-p_1)/(t_2-t_1) \quad (1)$$

A suitable rate of pressure increase to be applied to the airways of the patient 2 at or just after the inspiratory trigger point, $TP_{insp}$, may then be determined by the control unit 5 based on the so determined slope, $k_{PEI\_insp}$. For example, the control unit 5 may determine a suitable basic inspiratory pressure increase rate $k_{basic\_insp}$ that is proportional to the slope, $k_{PEI\_insp}$, of the $PEI_{insp}$ curve, and to control the pressure regulating means 3 so that the inspiratory pressure curve is given an average slope corresponding to said suitable basic inspiratory pressure increase rate, $k_{basic\_insp}$.

In another embodiment, the control unit 5 may store a look-up table wherein different ranges of values of the slope, $k_{PEI\_insp}$, of the $PEI_{insp}$ curve are associated with different basic inspiratory pressure increase rates $k_{basic\_insp}$, and select a suitable rate of pressure increase as the basic inspiratory pressure increase rate, $k_{basic\_insp}$, that is associated with the range comprising the calculated slope value, $k_{PEI\_insp}$.

Figure 6:
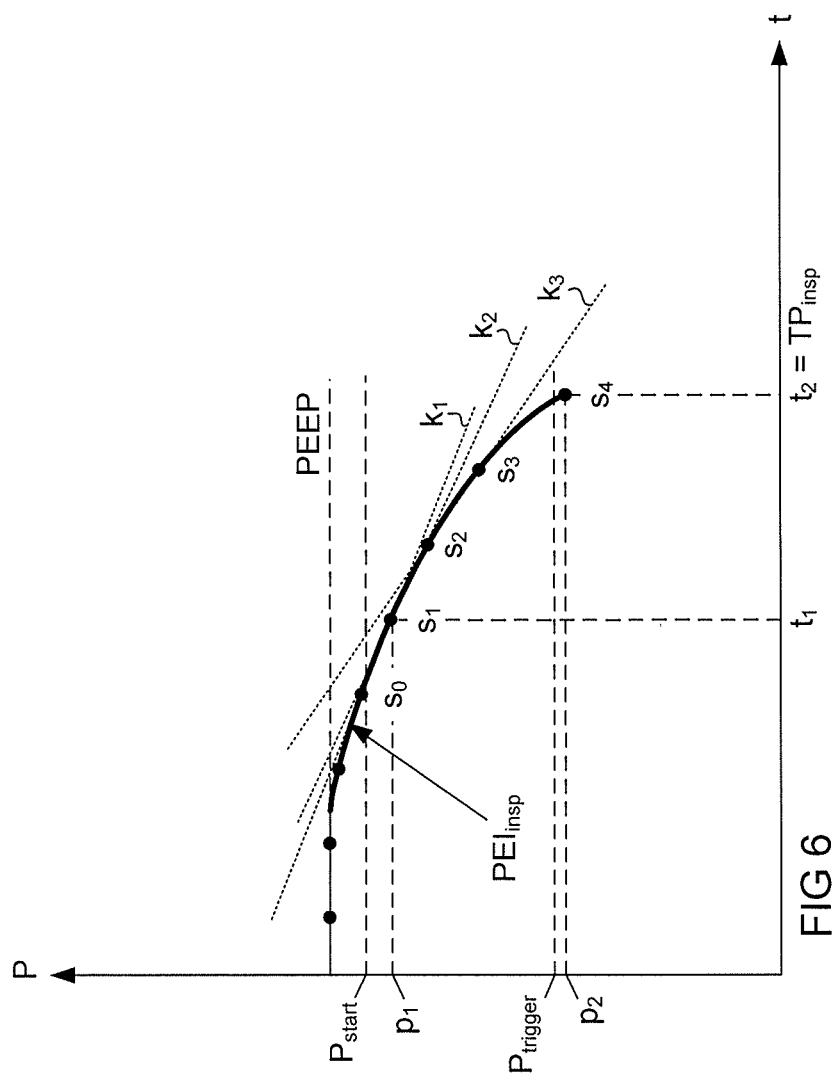

FIG. 6 illustrates another example of what the $PEI_{insp}$ curve may look like. Here it is seen that the $PEI_{insp}$ curve is non-linear and slightly convex. A convex $PEI_{insp}$ curve may be an indication that the patient's effort to inhale increases over time. Like in FIG. 5, the dots along the pressure curve illustrate sampled pressure values, obtained by the pressure sensor 4a of the breathing apparatus 1 illustrated in FIG. 1, and registered by the control unit 5. Some of the samples are seen to be denoted $s_0$-$s_4$.

In this embodiment, the control unit 5 is configured to continuously (i.e. repeatedly) calculate a current rate of change in the monitored pressure. This may be achieved by, for each registered sample, calculate the slope of a straight line between the registered pressure value and one or more of the previously registered pressure values. For example, when the control unit 5 registers a sample, $s_1$, having a pressure value falling below the first threshold value $P_{start}$, it may calculate the slope, $k_1$, of a straight line through the pressure values of the currently registered sample, $s_1$, and the previously registered sample, $s_0$. When the control unit 5 registers the next sample, $s_2$, it calculates the slope, $k_2$, of a straight line between the pressure value of this sample, $s_2$, and the pressure value of the previously obtained sample, $s_1$, and so on. The so calculated slopes, $k_1$-$k_3$, are hence approximations of the first derivative of $PEI_{insp}$ curve at a plurality of points along the curve.

The control unit 5 may further be configured to calculate, for each registered sample, a suitable rate with which the pressure applied to the airways of the patient should be increased upon detection of the inspiratory trigger point, $TP_{insp}$, i.e. a suitable inspiratory pressure increase rate. To calculate the suitable inspiratory pressure increase rate, the control unit 5 may use any of or any combination of the slope values, $k_1$-$k_3$. For example, the control unit 5 may be adapted to calculate an average slope of the $PEI_{insp}$ curve as the mean value of said slopes, and calculate a suitable basic inspiratory pressure increase rate (corresponding to $k_{basic\_insp}$ in any of FIGS. 3 to 5) that is proportional to said average slope. As described above, the control unit 5 may then control the pressure regulating means 3 to increase the inspiratory pressure in accordance with the so determined suitable basic inspiratory pressure increase rate at or just after the inspiratory trigger point, $TP_{insp}$.

Preferably, the control unit 5 is also configured to calculate one or more values indicative of the second derivative of the $PEI_{insp}$ curve, and to use this or these values in the calculation of the suitable inspiratory pressure increase rate. This may be achieved by comparing the slope values, $k_1$-$k_3$, with each other. For example, the control unit 5 may, when having determined a first and a second slope value, $k_1$ and $k_2$, calculate a value that is indicative of a second derivative of $PEI_{insp}$ as the difference (e.g. $k_2$-$k_1$) between these slope values. By establishing a trend for the first derivative of $PEI_{insp}$, the control unit 5 may hence retrieve information about the curvature (i.e. the second order derivative) of $PEI_{insp}$, and thereby determine whether the patient's effort to inhale seems to increase or decrease over time. The control unit 5 may also be configured to take higher order derivates of the $PEI_{insp}$ curve into account when calculating the suitable inspiratory pressure increase rate.

If the $PEI_{insp}$ curve is convex, indicating that the patient's effort to inhale increases over time, the control unit 5 may increase the inspiratory pressure increase rate to adjust it to needs of the patient, for example by calculating a suitable inspiratory pressure increase rate that is slightly higher than it would have been if the $PEI_{insp}$ curve was found to be linear. In a similar way, if the curvature of the $PEI_{insp}$ curve is concave, the control unit 5 can calculate a suitable inspiratory pressure increase rate that is slightly lower than it would have been if the $PEI_{insp}$ curve was found to be linear.

The control unit 5 of the breathing apparatus 1 may hence be configured to calculate an inspiratory pressure that is to be applied to the airways of the patient 2 at or just after the inspiratory trigger point, $TP_{insp}$, as a function of the monitored pressure and its derivative(s) at and/or just before the inspiratory trigger point. This means that the inspiratory pressure curve (IPC) may be expressed as:

$$IPC=f(p,\dot{p},\ddot{p},\ldots,p^n,t) \qquad (2)$$

where IPC is the inspiratory pressure applied to the airways of the patient during the initial phase of inspiration, p, $\dot{p}$, $\ddot{p}$, ..., $p^n$ is the monitored pressure and its derivatives at and/or just before the inspiratory trigger point, $TP_{insp}$, and t is time.

Furthermore, the control unit 5 is preferably configured to calculate the suitable rate of pressure increase prior to detection of the inspiratory trigger point, $TP_{insp}$, and to increase the pressure accordingly directly upon detection of the inspiratory trigger point. For example, the control unit 5 may be configured to calculate a suitable inspiratory pressure increase rate based on the slope value $k_1$ as soon as it registers the sample $s_1$, calculate a new or updated suitable inspiratory pressure increase rate based on both slope values $k_1$ and $k_2$ as soon as it registers the sample $s_2$, and calculate yet a new or updated suitable inspiratory pressure increase rate based on $k_1$, $k_2$ and $k_3$ as soon as it registers the sample $s_3$. When the control unit 5 registers the sample $s_4$ and detects that the inspiratory trigger condition is fulfilled, it does not calculate a new or updated suitable inspiratory pressure increase rate. Instead, it immediately starts to increase the pressure applied to the airways of the patient with a rate that is commensurate with the most recently calculated suitable inspiratory pressure increase rate.

Although FIGS. 5 and 6 and the description thereof relate to determination of a suitable inspiratory pressure increase rate based on the slope and/or curvature of the $PEI_{inep}$ curve, it should be appreciated that the same principles are applicable to determine a suitable expiratory pressure decrease rate based on the slope and/or curvature of the $PEI_{exp}$ curve.

Figure 7:
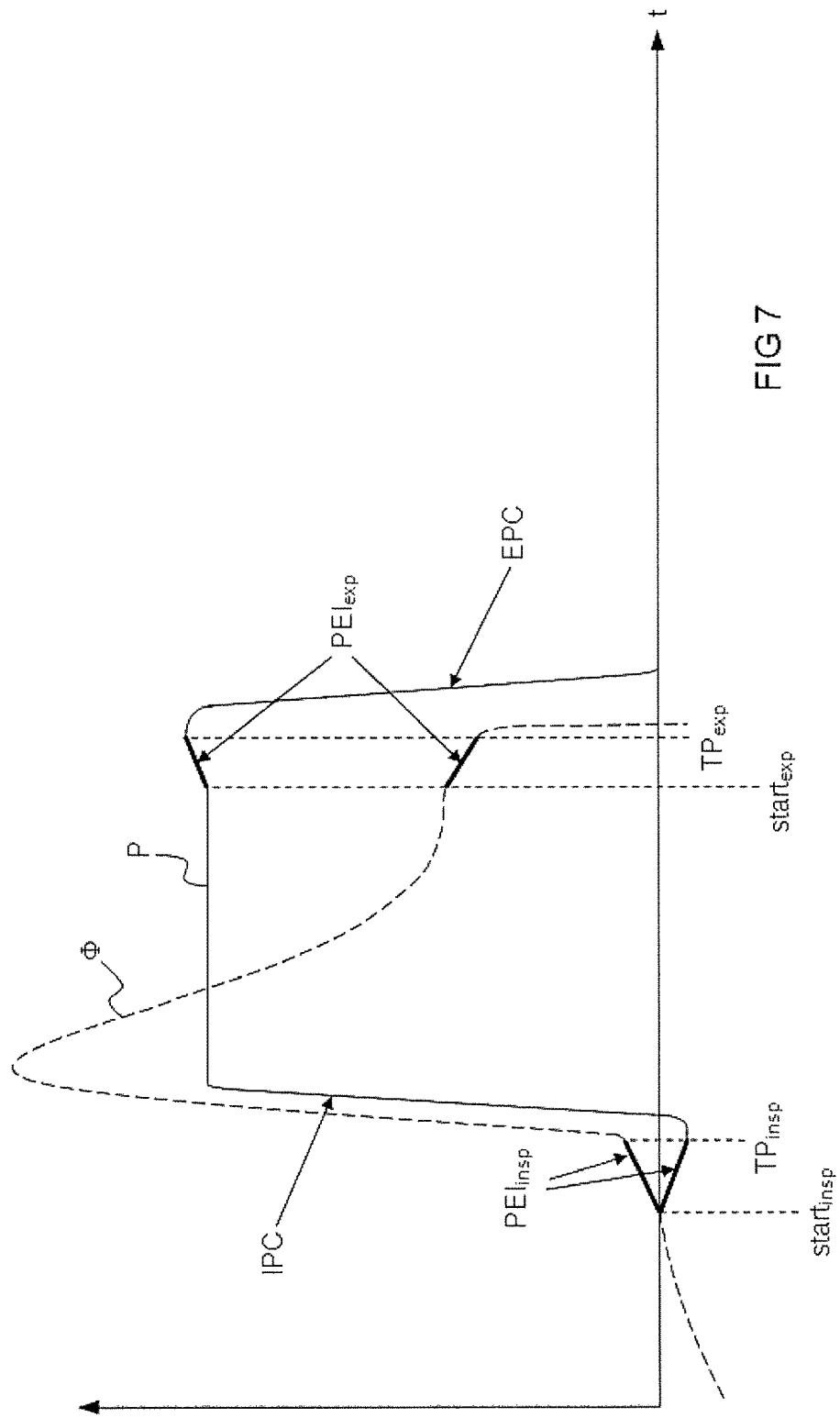
FIGS. 7 and 8 illustrate pressure and flow curves, obtained during a strong and weak breath, respectively.
Figure 8:
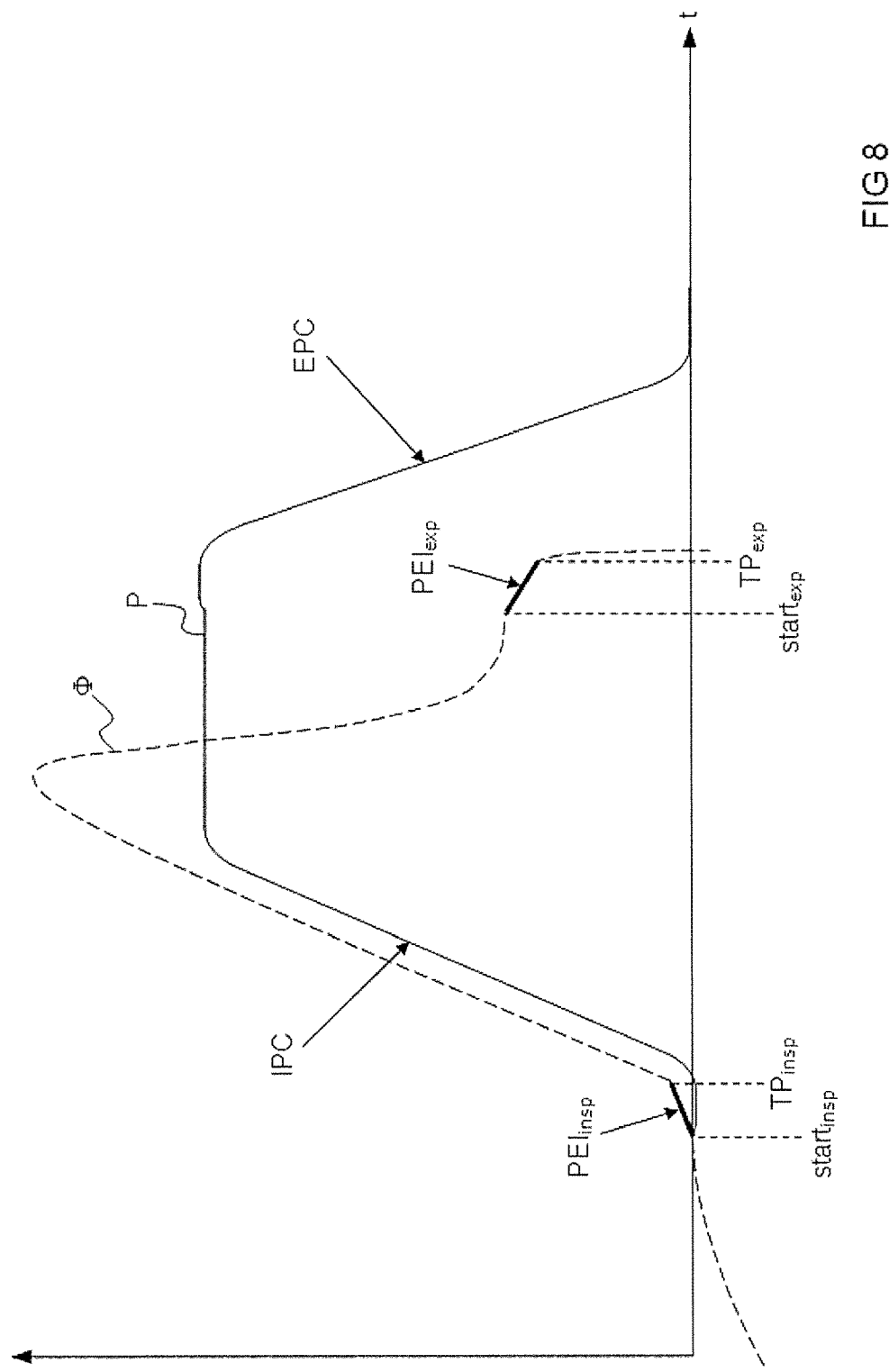

FIGS. 7 and 8 illustrate a pressure curve, P, as described above with reference to e.g. FIG. 2, and a flow curve, Φ, representing a measured or calculated flow substantially corresponding to the flow through the airways of a patient undergoing pressure supported ventilation. The flow curve, Φ, may for example be obtained by means of the flow sensors 4b, 4c arranged in the inspiratory line 6 and the expiratory line 9, respectively, of the breathing apparatus 1. FIG. 7 illustrates the pressure and flow curves obtained during a strong breath while FIG. 8 illustrates the pressure and flow curves obtained during a weak breath.

As illustrated in FIG. 7, a strong effort to inhale and exhale by the patient typically generates a distinct and easily measurable increase and decrease, respectively, in the monitored pressure, P. Likewise, the effort to inhale and exhale generates a distinct and easily measurable decrease and increase, respectively, in the monitored flow, Φ. Instead of or in addition to the rate of change in the monitored pressure, P, the control unit 5 of the breathing apparatus 1 may be configured to use the rate of change in the monitored flow, Φ, in the calculation of the suitable inspiratory pressure increase rate and/or the expiratory pressure decrease rate. Consequently, the flow curve segment between the point in time, $start_{insp}$, at which the patient 2 starts to inhale and the inspiratory trigger point, $TP_{insp}$, (possibly including one or both end points) may also be used by the control unit 5 as an indicator of the effort to inhale made by the patient, $PEI_{insp}$. In a corresponding way, the flow curve segment between the point in time, $start_{exp}$, at which the patient 2 starts to exhale and the expiratory trigger point, $TP_{exp}$, (possibly including one or both end points) may be used by the control unit 5 as an indicator of the effort to exhale made by the patient, $PEI_{exp}$.

It should be appreciated that the control unit 5 may determine the suitable inspiratory pressure increase rate and the suitable expiratory pressure decrease rate based on the slope and/or curvature of the $PEI_{insp}$ and the $PEI_{exp}$ of the flow curve, Φ, in ways corresponding to the ways of determining the suitable inspiratory pressure increase rate based on the slope and/or curvature of the $PEI_{insp}$ of the pressure curve, as described above with reference to FIGS. 2-6.

An advantage of using the monitored flow instead or in addition to the monitored pressure is that a weak effort to inhale or exhale is more easily detected. As illustrated in FIG. 8, a weak effort to inhale or exhale may cause no or a very small change in the monitored pressure while causing a rather distinct and fully measurable change in the monitored flow. That the change in monitored pressure, P, is small may be due to the fact that the change in pressure caused by an effort to inhale or exhale is small compared to the applied pressure, and/or very effective regulation of the pressure regulating means 3, which regulation counteracts pressure variations to maintain a constant PEEP during the final phase of expiration and a constant ITP during the final phase of inspiration.

Preferably, the breathing apparatus 1 has sensors 4*a-c* for monitoring both pressure and flow, and a control unit 5 that is configured to use any or both of the pressure and flow to determine the suitable rate of change in the pressure applied to the airways of the patient in the transitions between the respiratory phases.

The breathing apparatus 1 may further be adapted to apply the above described principles only for inspiratory pressure control, only for expiratory pressure control, or for both inspiratory and expiratory pressure control. In one embodiment, the breathing apparatus 1 may be adapted to use the principles only in order to tailor the pressure increase rate during the initial phase of inspiration to the patient's effort to inhale, while, when detecting the expiratory trigger point, $TP_{exp}$, indicating that the patient has made an attempt to exhale, simply decreasing the pressure applied to the airways of the patient as quickly as possible.

FIGS. 9A-B and 10A-B are flow charts illustrating the proposed method for providing support ventilation to a spontaneously breathing patient.

Figures 9A, 9B:
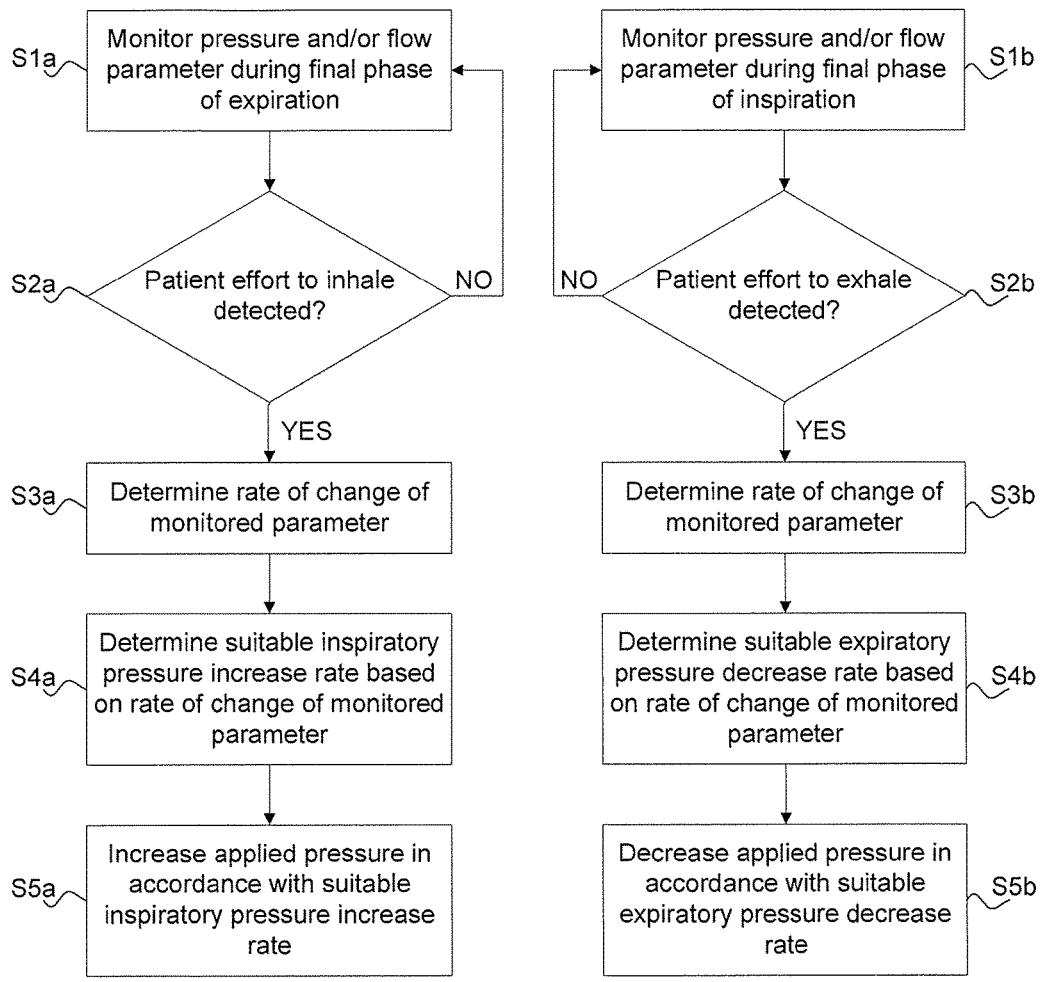
FIGS. 9A-B and 10A-B are flow charts illustrating exemplary embodiments of a method according to the invention.

FIG. 9A illustrates the basic principles of the proposed method for patient triggered inspiration. In first step, S1*a*, a pressure and/or flow is monitored during a final phase of expiration. In the next step, S2*a*, the monitored pressure and/or flow is analysed to determine whether the patient has made an effort to inhale. If an effort to inhale is detected, the method proceeds to step S3*a* in which a rate of change in the monitored pressure and/or flow is determined. In step S4*a*, a suitable inspiratory pressure increase rate is determined based on said rate of change in the monitored pressure and/or flow. In a final step, S5*a*, the pressure applied to the airways of the patient is increased in accordance with the suitable inspiratory pressure increase rate determined in step S4*a*.

FIG. 9B illustrates the basic principles of the corresponding method for patient triggered expiration. In a first step, S1*b*, a pressure and/or flow is monitored during a final phase of inspiration. In the next step, S2*b*, the monitored pressure and/or flow is analysed to determine whether the patient has made an effort to exhale. If an effort to exhale is detected, the method proceeds to step S3*b* in which a rate of change in the monitored pressure and/or flow is determined. In step S4*b*, a suitable expiratory pressure decrease rate is determined based on said rate of change in the monitored pressure and/or flow. In a final step, S5*b*, the pressure applied to the airways of the patient is decreased in accordance with the suitable expiratory pressure decrease rate determined in step S4*b*.

Figure 10A:
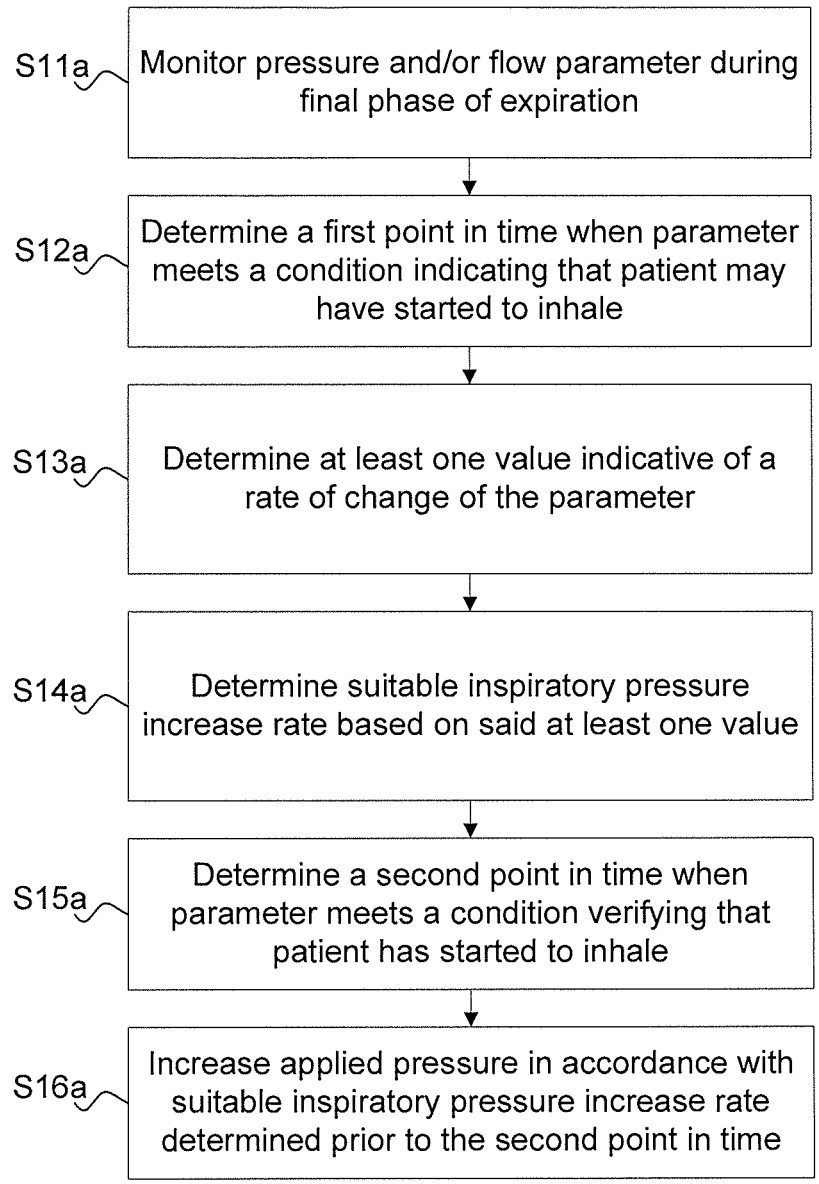

FIG. 10A illustrates a refined embodiment of the method for patient triggered inspiration illustrated in FIG. 9A. In a first step, S11*a*, a pressure and/or flow is monitored during a final phase of expiration. In the next step, S12*a*, a first point in time when the monitored pressure and/or flow meets a condition indicating that the patient may have started to inhale is determined. This first point in time corresponds to the point in time $t_1$ in FIGS. 5 and 6. In the next step, S13*a*, at least one value that is indicative of the rate of change of the monitored pressure and/or flow is determined. In step S14*a*, a suitable inspiratory pressure increase rate is determined based on said at least one value. In step S15*a*, a second point in time when the monitored pressure and/or flow meets a condition verifying that the patient has made an effort to inhale is determined. This second point in time corresponds to the inspiratory trigger point, $TP_{insp}$, in FIGS. 2-6. In a final step S16*a*, the pressure applied to the airways of the patient is increased in accordance with the suitable inspiratory pressure increase rate determined in step S14*a* and hence determined prior to the inspiratory trigger point, $TP_{insp}$.

Figure 10B:
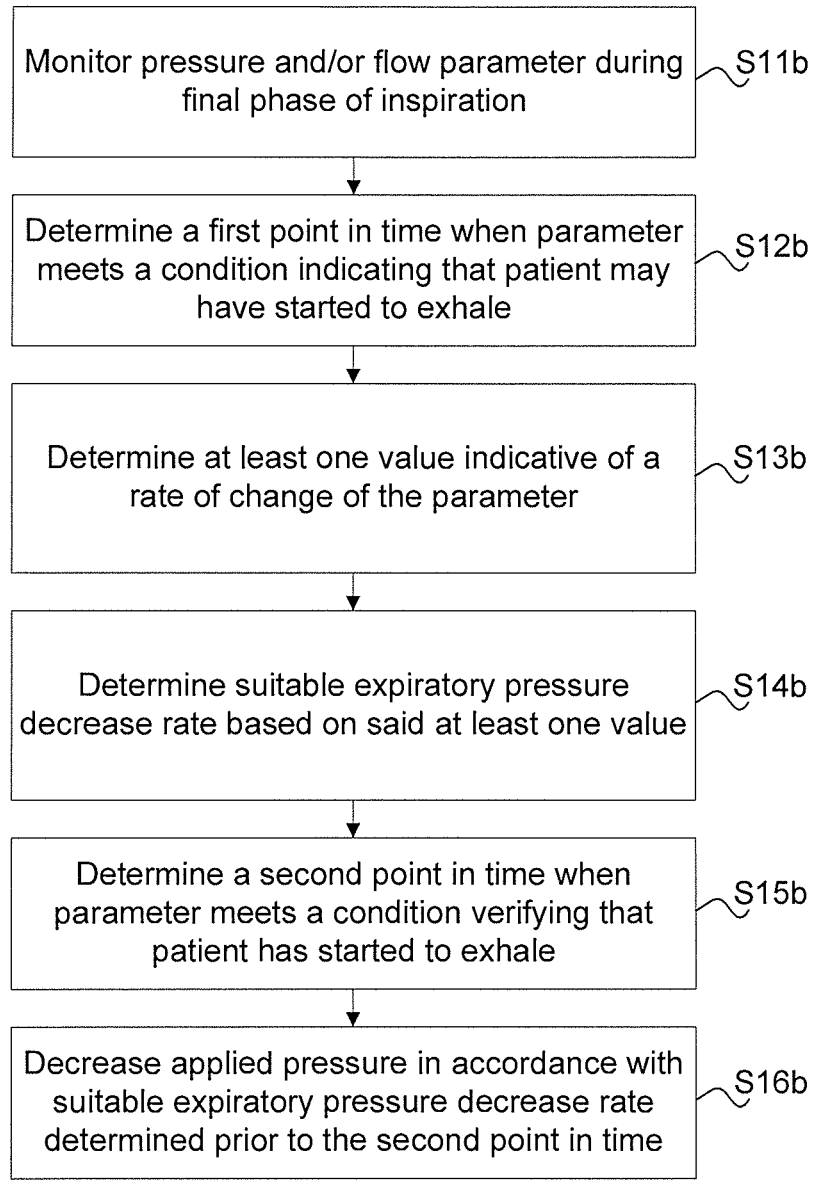

FIG. 10B illustrates a refined embodiment of the method for patient triggered expiration illustrated in FIG. 9B. In a first step, S11*b*, a pressure and/or flow is monitored during a final phase of inspiration. In the next step, S12*b*, a first point in time when the monitored pressure and/or flow meets a condition indicating that the patient may have started to exhale is determined. In the next step, S13*b*, at least one value that is indicative of the rate of change of the monitored pressure and/or flow is determined. In step S14*b*, a suitable expiratory pressure decrease rate is determined based on said at least one value. In step S15*b*, a second point in time when the monitored pressure and/or flow meets a condition verifying that the patient has made an effort to exhale is determined. This second point in time corresponds to the expiratory trigger point, $TP_{exp}$, in FIGS. 2-4. In a final step S16*b*, the pressure applied to the airways of the patient is decreased in accordance with the suitable expiratory pressure decrease rate determined in step S14*b* and hence determined prior to the expiratory trigger point, $TP_{exp}$.

Although modifications and changes may be suggested by those skilled in the art, it is the intention of the inventors to embody within the patent warranted heron all changes and modifications as reasonably and properly come within the scope of their contribution to the art.

We claim as our invention:

1. A breathing apparatus for providing support ventilation to a spontaneously breathing patient, comprising:
   a pressure regulator that regulates a pressure applied to airways of the patient;
   at least one pressure and/or flow sensor for obtaining pressure and/or flow measurements that are dependent on pressure or flow in the airways of the patient;

a control computer configured to monitor a pressure and/or flow based on said pressure and/or flow measurements;

the control computer being configured to detect a transition that occurs at a trigger point time between inhalation and exhalation by the patient or between exhalation and inhalation by the patient, based on a change in the monitored pressure and/or flow that occurs before said trigger point time;

the control computer being further configured to:

determine a suitable rate of change in the pressure applied to the patient based on the rate of the change in the monitored pressure and/or flow; and control the pressure regulator to change the applied pressure at or following said trigger point time in accordance with said suitable rate of change in response to said transition.

2. Breathing apparatus according to claim 1, wherein the control unit is configured to determine the suitable rate of change in applied pressure and to control the pressure regulator to change the applied pressure in accordance with said suitable rate of change on a breath-by breath basis.

3. Breathing apparatus according to claim 1, wherein the control unit is configured to change the applied pressure in accordance with the suitable rate of change upon detection of a trigger point, and to determine the suitable rate of change in applied pressure before detection of said trigger point.

4. Breathing apparatus according to claim 1, wherein the control unit is configured to determine the suitable rate of change in applied pressure also based on a change in the rate of change in the monitored pressure and/or flow.

5. Breathing apparatus according to claim 1, wherein the control unit is configured to control the pressure regulator to apply a substantially constant expiratory target pressure level at a end of an expiratory phase and a substantially constant inspiratory target pressure level at a end of an inspiratory phase, and to change the applied pressure between the expiratory target pressure level and the inspiratory target pressure level in accordance with said suitable rate of change.

6. Breathing apparatus according to claim 5, wherein the control unit is configured to determine a suitable rate of change in applied pressure which varies in time and accelerates during a first time period of an initial phase of the inspiratory or expiratory phase and decelerates during a second time period of the initial phase of the inspiratory or expiratory phase.

7. Breathing apparatus according to claim 1, wherein the control unit is configured to determine a basic value for the suitable rate of change in the applied pressure, fit a pressure curve to a straight line having a slope corresponding to said basic value, and change the applied pressure in accordance with said pressure curve.

8. A method for providing support ventilation to a spontaneously breathing patient, comprising:

placing airways of a patient in communication with a pressure regulator, operating the pressure regulator so as to regulate a pressure applied to the airways of the patient;

in a control computer, monitoring a pressure and/or flow based on pressure and/or flow measurements that are dependent on pressure or flow in the airways of the patient;

in said control computer, detecting a transition that occurs at a trigger point time between inhalation and exhalation by the patient or between exhalation and inhalation by the patient, based on a change in the monitored pressure and/or flow that occurs before said trigger point time;

in said control computer, determining a rate of change in a pressure applied to the patient based on the rate of the change in the monitored pressure and/or flow; and in said control computer generating control signals, and emitting control signals to said pressure regulator, in order to operate the pressure regulator so as to change the applied pressure at or following said trigger point time in accordance with said suitable rate of change in response to said effort to inhale or exhale.

9. Method according to claim 8, wherein said method is performed on a breath-by breath basis.

10. Method according to claim 8, comprising detecting a trigger point indicating that the patient has made an effort to inhale or exhale and changing the applied pressure upon detection of said trigger point, the determination of the suitable rate of change in applied pressure being made prior to detection of said trigger point.

11. Method according to claim 8 comprising making the determination of the suitable rate of change in applied pressure also based on a change in the rate of change in the monitored pressure and/or flow.

12. Method according to claim 8 comprising:

applying a substantially constant expiratory target pressure level at the end of an expiratory phase;

applying a substantially constant inspiratory target pressure level at the end of an inspiratory phase; and changing the applied pressure between the expiratory target pressure level and the inspiratory target pressure level in accordance with said suitable rate of change.

13. Method according to claim 12, comprising changing the applied pressure such that the rate of change accelerates during a first time period of an initial phase of the inspiratory or expiratory phase and decelerates during a second time period of the initial phase of the inspiratory or expiratory phase.

14. Method according to claim 8, further comprising:

determining a basic value for the suitable rate of change in the applied pressure;

fitting a pressure curve (IPC, EPC) to a straight line having a slope corresponding to said basic value; and changing the applied pressure in accordance with said pressure curve (IPC, EPC).

15. A non-transitory, computer-readable data storage medium encoded with programming instructions, said storage medium being loaded into a computerized processor of a breathing apparatus that provides support ventilation to a spontaneously breathing patient, said breathing apparatus also comprising a pressure regulator that is in communication with airways of the patient, and at least one pressure and/or flow sensor, said programming instructions causing said computerized control unit to:

operate the pressure regulator to regulate a pressure applied to the airways of the patient;

monitor a pressure and/or flow based on pressure and/or flow measurements made by said sensor that are dependent on pressure or flow in the airways of the patient;

detect a transition that occurs at a trigger point time between inhalation and exhalation by the patient or between exhalation and inhalation b the patient, based on a change in the monitored pressure and/or flow that occurs before said trigger point time;

determine a rate of change in a pressure applied to the patient based on the rate of the change in the monitored pressure and/or flow; and operate the pressure regulator to change the applied pressure at or following said trigger point time in accordance with said suitable rate of change in response to said effort to inhale or exhale.

* * * * *